United States Patent [19]

Dioguardi

[11] Patent Number: 5,198,465
[45] Date of Patent: Mar. 30, 1993

[54] COMPOSITIONS BASED ON AMINO ACIDS FOR PREVENTING AND TREATING PRECURSOR DEFICIENCIES IN THE SYNTHESIS OF COLLAGEN

[76] Inventor: Francesco S. Dioguardi, Via Ciovasso, 11, 20121 Milan, Italy

[21] Appl. No.: 717,464

[22] Filed: Jun. 19, 1991

[51] Int. Cl.⁵ ................. A61K 31/34; A61K 31/19
[52] U.S. Cl. ................. 514/474; 514/557; 514/801; 424/417
[58] Field of Search ........ 424/195.1; 530/356; 514/801, 474, 557

[56] References Cited

U.S. PATENT DOCUMENTS 4,357,343  11/1982  Madsen et al. .................. 514/400

OTHER PUBLICATIONS

T. F. Linsenmayer, Cell Biology of Extracellular matrix, Chap. 1, 5–37, 1982.
Bjorn Reino Olsen, Cell Biology of Extracellular Matrix, Chap. 6, 139–177, 1982.
A. Chamson et al., Clin. Physiol. Biochem., 7, 128–136, 1989.
L. Stryer, Biochemistry, Chap. 9, 185–189, 1981.

Primary Examiner—Johnnie R. Brown
Assistant Examiner—A. Varma
Attorney, Agent, or Firm—Birch, Stewart, Kolasch & Birch

[57] ABSTRACT

A composition based on aminoacids and free from hydroxy-proline or hydroxy-lysine useful for preventing and treating precursors deficiencies in the synthesis of collagen comprising proline, glycine, lysine, vitamin C, and one or more compounds selected in the group consisting of α-ketoglutaric acid, methionine, cysteine, cystine, valine as well as pharmaceutically acceptable diluents and excipients is described.

9 Claims, No Drawings

COMPOSITIONS BASED ON AMINO ACIDS FOR PREVENTING AND TREATING PRECURSOR DEFICIENCIES IN THE SYNTHESIS OF COLLAGEN

PRIOR ART

Collagen is a family of fibrous proteins which forms about one fourth of the total body content in mammals. Collagen is ubiquitous and is the main fibrous component of skin, bone, tendons, cartilage, blood vessels and teeth.

Aminoacids that can be found in collagen, are mainly glycine (30% of all aminoacids), hydroxyproline (OH-proline), proline and hydroxylysine (OH-lysine).

In many tissues there is, associated with collagen, elastin, which is similar to collagen, but characterized by the presence of a high content of valine molecules in the amino acid chain.

OH-proline and OH-lysine of alimentary origin are not suitable for the synthesis of collagen, because only the hydroxylation of proline and lysine by two specific enzymes (proline hydroxylase and lysine hydroxylase) allows to proceed the synthesis of collagen in vivo. In turn, these enzymes need vitamin C to be activated, and lysine hydroxylase also requires an adequate amount of α-keto glutarate.

Scurvy induces alterations of joints and ligaments due to a cessation of collagen synthesis by cutting off of the reactions catalyzed by vitamin C, which is lacking in scurvy.

Obviously, all biological conditions of elevated vitamin C consumption (smoke, pregnancy, strenuous physical activity) or reduced introduction, although with less evident manifestations, can be considered situations in which collagen synthesis in the skin and in all the other sites is reduced. On the other hand, peptides containing OH-lysine or OH-proline, as in products derived by collagen hydrolisis, are strongly inhibitory for collagen synthesis.

It must be understood that, in any case, the limiting factor of collagen synthesis is the bioavailability of precursors into the fibroblasts (collagen synthesizing cells).

Proline is probably the main limiting factor, due to its low concentration in the plasma and to the reduced amount that can be introduced with foods. Therefore, insufficient introduction or elevated consumption for other purposes (e.g. neoglucogenesis), can induce a reduction of proline plasma concentrations, as happens in athletes (see table 1), who are individuals with joint and ligament stresses obviously higher than those for normal sedentary people.

TABLE 1

Modifications of proline blood concentrations during strenuous physical activity. (mg/l)

|  | proline concentrations before training | proline concentrations after 1 hour training |
|---|---|---|
| case 1 | 6.55 | 4.38 |
| case 2 | 7.73 | 5.40 |
| case 3 | 6.70 | 5.60 |
| case 4 | 6.85 | 6.65 |
| case 5 | 16.10 | 10.66 |
| case 6 | 7.60 | 6.65 |
| case 7 | 7.45 | 6.50 |
| case 8 | 10.80 | 6.24 |
| case 9 | 6.94 | 5.58 |
| case 10 | 7.20 | 6.70 |

DETAILED DESCRIPTION OF THE INVENTION

We have found compositions that can enhance the synthesis of collagen in humans, largely overcoming the problems encountered up to now and suitable for topical or systemic administration. The compositions of the invention are particularly useful for the treatment of collagen synthesis in all conditions where an increased turnover or a reduced synthesis due to a lack of precursors or of the coenzymes of the collagen metabolic pathway.

The invention's compositions are based on aminoacids and are free from hydroxy-proline or hydroxy-lysine and are useful for preventing and treating precursor deficiencies in the synthesis of collagen which compositions comprise proline, glycine, lysine, vitamin C, and one or more compounds selected in the group consisting of α-ketoglutaric acid, methionine, cysteine, cystine, valine as well as pharmaceutically acceptable diluents and excipients.

The characteristics and advantages of the compositions for preventing and treating precursor deficiencies in the synthesis of collagen according to the present invention will be set forth in the following detailed description.

The pharmaceutically acceptable diluents and excipients suitable for the compositions of the invention are dependent upon the chosen way of administration, which can be either topic (i.e. dermatological) application or systemic administration (mainly oral use). Preferred excipients and diluents for topical administration are liposomes, Essex cream, glycerine, spermaceti oil, octanoic and decanoic esters of saturated fatty alcohols having from 12 to 18 C atoms, isopropilic acid.

Preferred excipients and diluents for systemic administration are lactose, maize starch, cellulose and deionized water. The compositions for topical application contains the following percentages by weight of the various components:

| | |
|---|---|
| proline | from 10 to 50% |
| glycine | from 10 to 50% |
| lysine | from 10 to 50% |
| vitamin C | from 0.1 to 50% |
| methionine or cystine or cysteine or valine | from 0.1 to 20% |
| alpha-ketoglutaric acid | from 0 to 20% | and diluents and excipients in a weight ratio higher than 100% of the weight of the sum of the other components.

These compositions are suitable for the treatment of all conditions in which there is an altered local synthesis of connective tissue, as happens when the so called cellulitis results from hormonal imbalances due to adolescence, or when pregnancy and when taking the birth control pill, plastic surgery scars, burns, bed-sores, and diabetic torpid ulcerations interfere with normal collagen synthesis.

Compositions suitable for oral use have the same content of aminoacids and vitamin C as those for topical use, but with a lower content of excipients and diluents. The compositions for systemic use have the following indications:

together with topical administration in all conditions in which such topic use is proper;

for the prevention of dermal aging in subjects exposed to physical injuries such as UV rays, cold, and the sun;

when and where there is an increased requirement of collagen synthesis, as happens in athletes having strained tendons and ligaments;

in dysthrophic joint pathologies (arthrosis).

The topical uses of these compositions were tested on 5 young women, who had undergone microinjection of collagen into some face wrinkles, for esthetic purposes.

| | |
|---|---|
| proline | 10 parts by wt. |
| glycine | 50 parts by wt. |
| lysine | 10 parts by wt. |
| vitamin C | 5 parts by wt. |
| methionine | 2 parts by wt. |
| alpha-ketoglutaric acid | 5 parts by wt. |
| diluents and excipients | 740 parts by wt. |

The application twice a day of the above composition induced an increased lasting of the aesthetic implantation and a less frequent need of re-injection.

Table 2 reports the intervals between injections, without and of the topic treatment with the compositions according to the invention.

TABLE 2

Intervals in weeks between intradermal microinjections of collagen (data are expressed as the average of 2 observations)

| | without treatment | with treatment |
|---|---|---|
| case 1 | 7 | 12 |
| case 2 | 8 | 15 |
| case 3 | 8 | 14 |
| case 4 | 7 | 9 |
| case 5 | 9 | 16 |

The compositions for systemic use were tested by oral administration to 12 athletes of similar weight.

They were given about 1 g/Kg of body weight per day, corresponding to 5 grams of proline a day, of the following composition:

| | |
|---|---|
| proline | 10 parts by wt. |
| glycine | 50 parts by wt. |
| lysine | 10 parts by wt. |
| vitamin C | 0.1 parts by wt. |
| methionine | 2 parts by wt. |
| diluents and excipients | 26 parts by wt. |

A further amount of vitamin C of 2 g/day for person was separately administered.

The control of absorption was followed through the measurement of proline concentration in blood.

Data are reported in Table 3.

TABLE 3

Proline blood concentrations in 12 athletes, before (basal) and after oral load of 5 grams of proline (mean ± standard deviation).

| TIME | mg/l |
|---|---|
| Basal | 6.8 ± 4.8 |
| 30' | 13.7 ± 6.3 |
| 60' | 15.9 ± 9.1 |
| 120' | 10.2 ± 7.4 |
| 240' | 7.1 ± 4.7 |

All athletes complained of knee or elbow pain, although they had been treated with anti-inflammatory drugs. After 6 weeks, no more complaint of joint pains were reported by any athlete, although the training programs had not been changed.

I claim: m

1. A composition free from hydroxy-proline and hydroxy-lysine and useful for treating precursor deficiencies in the synthesis of collagen consisting of 10 to 50% proline, 10 to 50% glycine, 10 to 50% lysine, 0.1 to 50% vitamin C, and one or more compounds in amounts of 0.1 to 20% and selected from the group consisting of α-ketoglutaric acid, methionine, cysteine, cystine, and valine, as well as pharmaceutically acceptable diluents and excipients.

2. A composition according to claim 1, suitable for topic application, wherein the amount of diluents and excipients is in a weight ratio higher than 100% of the weight of the sum of the other components.

3. A composition suitable for topic application and free from hydroxy-proline and hydroxy-lysine and useful for treating precursor deficiencies in the synthesis of collagen which consists of proline 10 parts by wt.; glycine 50 parts by wt.; lysine 10 parts by wt.; vitamin C 5 parts by wt.; one or more compounds selected from the group consisting of α-ketoglutaric acid, methionine, cystine, cystine and valine being 7 parts by wt. and the amount of diluents and excipients being 740 parts by wt.

4. A composition according to claim 1 wherein said diluents and excipients are one or more compounds selected from the group consisting of liposomes, Essex cream, glycerine, spermaceti oil, octanoic and decanoic saturated fatty alcohols having from 12 to 18 C atoms, and isopropilic acid.

5. A composition according to claim 1 suitable for oral administration, wherein the amount of diluents and excipients is in a weight ratio higher than 30% of the weight of the sum of the other components.

6. A composition suitable for oral administration and free from hydroxy-proline and hydroxy-lysine and useful for treating precursor deficiencies in the synthesis of collagen which consists of proline 10 parts by wt.; glycine 50 parts by wt.; lysine 10 parts by wt.; vitamin C 0.1 parts by wt.; one or more compounds selected from the group consisting of α-ketoglutaric acid, methionine, cysteine, cystine and valine being 2 parts by wt., and the amount of diluents and excipients being 26 parts by wt.

7. A composition according to claim 2 wherein said diluents and excipients are one or more compounds selected in the group consisting of lactose, maize starch, cellulose and distilled water.

8. A composition free from hydroxy-proline and hydroxy-lysine, useful for treating precursor deficiencies in the synthesis of collagen consisting of 10 to 50 parts by wt. of proline, 10 to 50 parts by wt. of glycine, 10 to 50 parts by wt. of lysine, vitamin C, and one or more compounds selected from the group consisting of α-ketoglutaric acid, methionine, cysteine, cystine, valine, as well as pharmaceutically acceptable diluents and excipients.

9. A pharmaceutical composition free from hydroxy-proline and hydroxy-lysine, useful for treating the precursor deficiencies in the synthesis of collagen consisting of 10 to 50 parts by wt. of proline, 10 to 50 parts by wt. of glycine, 10 to 50 parts by wt. of lysine, 0.1 to 50 parts by wt. of vitamin C, and 0.1 to 20 parts by wt. of one or more compounds selected from the group consisting of α-ketoglutaric acid, methionine, cysteine, cystine, and valine, and pharmaceutically acceptable diluents and excipients. n

* * * * *